US00PP26322P3

(12) United States Plant Patent
Suphachadiwong

(10) Patent No.: US PP26,322 P3
(45) Date of Patent: Jan. 19, 2016

(54) *VANDA* PLANT NAMED 'SPCDW1205'

(50) Latin Name: *Vanda hybrid.*
Varietal Denomination: SPCDW1205

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 172 days.

(21) Appl. No.: 13/987,934

(22) Filed: Sep. 16, 2013

(65) Prior Publication Data

US 2014/0082796 P1 Mar. 20, 2014

(30) Foreign Application Priority Data

Sep. 17, 2012 (QZ) ..... PBR 2012/1954

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Cassandra Bright

(57) ABSTRACT

A new and distinct *Vanda* cultivar named 'SPCDW1205' is disclosed, characterized by a large, heavily patterned greyed-purple colored flower. The new variety is a *Vanda*, typically produced as an indoor ornamental plant.

2 Drawing Sheets

Figure 1:
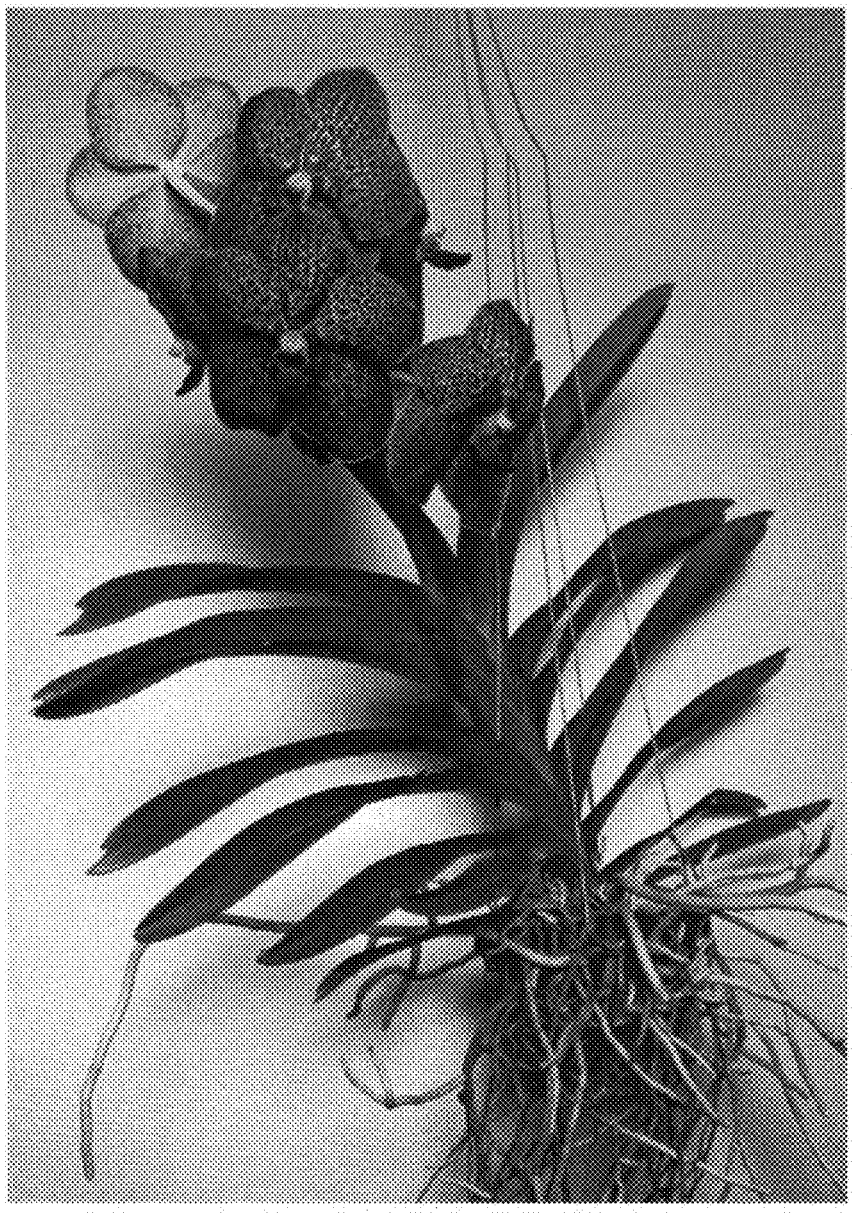

Latin name of the genus and species: *Vanda* hybrid.
Variety denomination: 'SPCDW1205'.

BACKGROUND OF THE INVENTION

This application relates to a new cultivar of *Vanda* hybrid and claims priority to EU application 2012/1954 filed Sep. 17, 2012. The new variety is the product of a planned breeding program. The new variety originated as a seedling from the crossing of the unpatented, proprietary seed parent *Vanda* 'M02' with the unpatented, proprietary pollen parent referred to as *Vanda* 'M58'. The crossing was made by the inventor in his research greenhouse in Chonburi, Thailand in January of 1989.

The new variety was first selected by the inventor, Thumrong Suphachadiwong, a citizen of Thailand, in September of 1993 in a research greenhouse belonging to the inventor in Chonburi, Thailand. After identifying the new variety as a potentially interesting selection, the inventor continued confidential testing and propagation of 'SPCDW1205', assessing stability of the unique characteristics of this variety.

Asexual reproduction of the new cultivar 'SPCDW1205' was first performed at a commercial laboratory belonging to the inventor in Chonburi, Thailand by tissue culture in February of 2007. Tissue culture propagation was performed using the base of leaves. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1205' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1205.' These characteristics in combination distinguish 'SPCDW1205' as a new and distinct *Vanda* cultivar:

1. Flowers with a white background, very heavily dotted greyed-purple.
2. Large flowers.
3. Purple to greyed-purple lip color.

PARENT COMPARISON

Plants of the new cultivar 'SPCDW1205' are similar to the seed parent, *Vanda* 'M02' in most horticultural characteristics. However the new variety, 'SPCDW1205' differs from 'M02' in the following characteristics:

1. Flowers of the new variety are have a patterned coloration, flowers of the parent variety are solid colored.

Plants of the new cultivar 'SPCDW1205' are similar to the pollen parent, *Vanda* 'M58' in most horticultural characteristics. However the new variety, 'SPCDW1205' differs from 'M58' in the following characteristics:

1. Larger flower size.
2. Different flower color.

COMMERCIAL COMPARISON

'SPCDW1205' is similar in most horticultural characteristics to the unpatented commercial variety *Vanda* 'Black Magic' in most horticultural characteristics. However the new variety, 'SPCDW1205' differs from 'Black Magic' in the following characteristics:

1. Flower color is red. Comparator flower color is dark purple.
2. Slightly darker leaf color.

BRIEF DESCRIPTION OF THE PHOTOGRAPHS

The accompanying photograph in FIG. 1 illustrates in full color a typical plant of 'SPCDW1205' grown in a commercial greenhouse in Honselersdijk, the Netherlands. The plant is 5½ to 6½ years old. Plant is growing in a hanging basket without soil.

Figure 2:
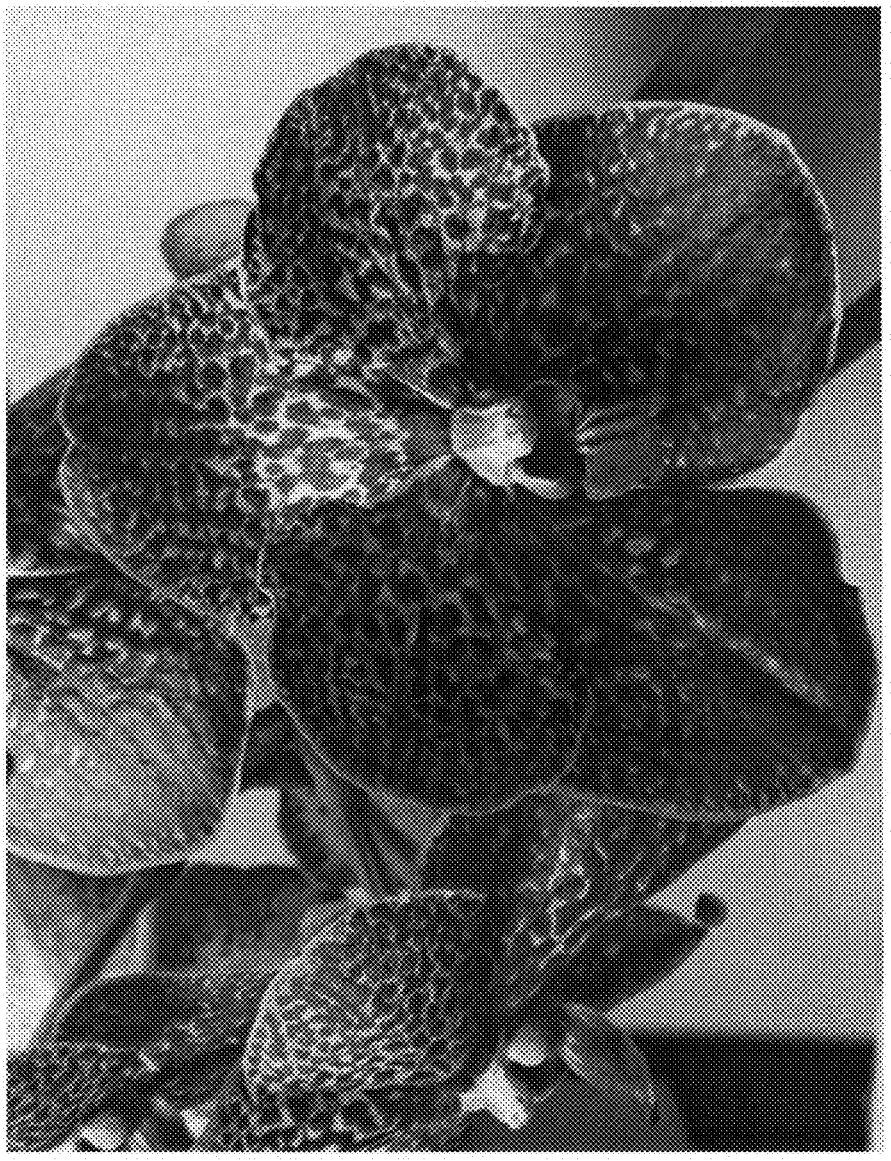

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1205' plants grown in a commercial greenhouse in Honselersdijk, the Netherlands. The plant is 5½ to 6½ years old. Described plant is growing in a hanging basket without soil. Temperatures ranged between 19° C. and 23° C. day and night. No photoperiodic or chemical treatments were given to the plants. During bright Summer conditions, shade was given. During dark Winter months, no supplemental light was given. Measurements and numerical values represent averages of typical plant types.

Botanical classification: *Vanda* hybrid 'SPCDW1205'.

PROPAGATION

Type of propagation typically used: Tissue culture propagation was performed using the base of leaves.

Time to produce a rooted cutting/liner: The time needed from for the start of a mericlone to get the small plants ready for deflasking is approximately 24 months under a controlled temperature of about 26 degrees Celsius. After that period plantlets have mature roots. Plants start to make roots in the last 6 months in flasks.

Root description: Moderately to heavy rooting with aerial roots only. Roots very fleshy, non-fibrous. Average length of old roots: 33.7 cm, average diameter of old roots (mature, now ineffective): 0.2 mm, average diameter of young roots (mature, vital): 0.4 cm. Old roots colored yellow-green; near RHS 147B. Young roots colored greyed-green; near RHS 192C to 192D, growing tips of roots yellow-green; 152A. Roots are located at the base of the stem, growing from approx. the lowest 25% of the stem.

PLANT

Growth habit: Monopodial, upright.

Height from soil line to top of foliage: Average height from base (plant grown in hanging basket, so no soil line present) to top of flowers: 42.8 cm.

Plant spread: Average: 49.5 cm.

Normal pot size: Hanging basket (8×8 cm square).

Growth rate: Moderate.

Number of leaves per plant: Average: 25.

FOLIAGE

Leaf:

- *Arrangement*.—Distichous.
- *Average length*.—Approximately 25.1 cm.
- *Average width*.—Approximately 2.9 cm.
- *Shape of blade*.—Ligulate, strongly carinate.
- *Aspect*.—Slightly curved.
- *Apex*.—Unequal praemorse.
- *Base*.—Sheathing. Sheath length: Average 1.9 cm. Sheath width: Average 1.5 cm. Sheath color: Yellow-green; near RHS 146A and 146B.
- *Margin*.—Entire.
- *Texture of top surface*.—Glabrous, very slightly glossy.
- *Texture of bottom surface*.—Glabrous, matte.
- *Color*.—Young foliage upper side: Green; near RHS 143A but darker. Young foliage under side: Green to yellow-green; a color in between near RHS 143A and 144A. Mature foliage upper side: Green; near RHS N137A but slightly darker. Mature foliage under side: Green to yellow-green; a color in between near RHS 143A and 144A.
- *Venation*.—Type: Parallel. Venation coloration: As leaf surface; upper side: green; near RHS N137A but darker, lower side: green to yellow-green; a color in between near RHS 143A and 144A.

Petiole: No petioles present, leaves sessile.

FLOWERING CHARACTERISTICS

Flower bud:

- *Rate of opening*.—Buds open approx. three weeks from emergence.
- *Length*.—Average: 1.7 cm.
- *Diameter*.—Average: 1.6 cm.
- *Shape*.—Near globular to deltoid.
- *Color*.—Yellow-green; near RHS 145A, dotted greyed-purple; near RHS 187A.

Peduncle:

- *Length*.—Approximately 37.2 cm.
- *Width*.—Approximately 0.7 cm.
- *Aspect*.—Approximately 40° angle to rosette.
- *Strength*.—Strong.
- *Texture*.—Smooth, moderately glossy.
- *Color*.—Yellow-green; near RHS 144A.

Inflorescence:

- *Flowers per stem*.—Average: 14.
- *Stem diameter*.—1.1 cm.
- *Inflorescence arrangement*.—Axially placed raceme.
- *Inflorescence height*.—Approximately 20.1 cm (measured from base of lowest flower to top of upper flower).
- *Inflorescence width*.—Approximately 17.9 cm.
- *Inflorescence orientation*.—Obliquely upward.

Individual flowers:

- *Flower type*.—Zygomorphic (orchidaceous), typical shape for the genus *Vanda*.
- *Shape*.—Zygomorphic, consisting of three sepals and three petals, one of which is transformed into a labellum (lip).
- *Length* (*height*).—Approximately 10.1 cm.
- *Width*.—Approximately 9.3 cm.
- *Depth*.—Approximately 3.5 cm.
- *Fragrance*.—No fragrance.
- *Persistent*—No.
- *Quantity of petals*.—3 (2 "traditional" petals and a labellum (lip), described separately).
- *Lastingness of flowers on the plant*.—6 weeks (from opening of flower to falling off).
- *Flower orientation*.—Outwards, towards all directions.

Petals:

*Arrangement*.—One lateral petal on each side.

*Length*.—Approximately 4.5 cm.

*Width*.—Approximately 4.3 cm.

*Shape*.—Near orbicular to broad ovate.

*Apex*.—Obtuse.

*Base*.—Cuneate.

*Margin*.—Entire, slightly undulate.

*Texture*.—Upper forward surface: Glabrous, matte, velvety.

*Texture*.—Lower back surface: Glabrous, matte, velvety.

*Color*.—When opening, forward surface: White to yellow; in between near RHS 155A to 155B and 11D, base greyed-purple; 184B, petal heavily dotted greyed-purple; near RHS 187C to 187D. When opening, back surface: White to green-white; near RHS 155A and 157D, margin greyed-purple; near RHS 186C, moderately dotted greyed-purple near the margin; near RHS N186D. Fully Opened, forward surface: White; near RHS 155A, heavily dotted greyed-purple; near RHS 187C to 187D. Fully Opened, back surface: Greyed-green; near RHS 198D, margin greyed-purple; near RHS 185C to 185D, moderately dotted greyed-purple near the margin; near RHS 187B to 187C. Fading, forward surface: Not fading. Fading, back surface: Not fading.

*Color venation fully opened, forward surface*.—Other veins are not visible as such but colored as the forward surface. In parts where the surface color is 155A, the veins are also; in parts where the surface color is 187C, the veins are also; in parts where the surface color is 187D, the veins are also.

*Color venation fully opened, back surface*.—Main vein tinged purple; near RHS 76A, the other veins are not visible as such but colored as the forward surface. In parts where the surface color is 155A, the veins are also; in parts where the surface color is 187C, the veins are also; in parts where the surface color is 187D, the veins are also.

Labellum/lip:

*Shape*.—Three-lobed, lateral lobes involute, central lobe slightly revolute.

*Length*.—Lateral lobe length: Approximately 1.1 cm. Lateral lobe width: Approximately 0.9 cm. Central lobe length: Approximately 2.3 cm. Central lobe width: Approximately 1.4 cm.

*Width*.—Approximately 1.4 cm.

*Texture*.—Glabrous, slightly glossy, with 3 callosities.

*Central lobe*.—Emarginate tip (apex).

*Lateral lobes*.—Have obtuse tips (apices).

*Base* (*where central lobe attaches to spur*).—Cuneate.

*Color*.—When opening, forward surface: Lateral lobes yellow-green; near RHS 150C. Central lobe red-purple; near RHS 71 A, central lobe of the labellum, including callosities; near RHS N79B, base and callosities white to greyed-white; in between near RHS N155B and 156D. When opening, back surface: Lateral lobes green-white; near RHS 157A, striped very light greyed-red; near RHS 182D. Central lobe purple; near RHS 77A, lower half green-white; near RHS 157A. Fully Opened, forward surface: Lateral lobes greyed-green; near RHS 196B, striped purple; near RHS N77C. Central lobe purple to greyed-purple; in between near RHS 79A and N186C, callosities greyed-white; near RHS 156C to 156D. Fully Opened, back surface: Lateral lobes yellow-green; near RHS 152D, striped greyed-green; near RHS 195A. Central lobe purple; near RHS 79A, lower half greyed-green; near RHS 195B. Fading, forward surface: Not fading. Fading, back surface: Not fading.

*Color venation fully opened, forward surface*.—No venation visible on labellum.

*Color venation fully opened, back surface*.—No venation visible on labellum.

*Margin of the labellum*.—Central Lobe: Entire. Lateral Lobe: Entire.

Spurs:

*Quantity*.—Average: 1.

*Appearance*.—Short triangular, in line with central lobe of labellum.

*Length*.—Approximately 0.7 cm.

*Width*.—Approximately 0.5 cm.

*Height*.—Approximately 0.7 cm (at the base).

*Shape*.—Short triangular.

*Apex*.—Obtuse.

*Base*.—Broad cuneate.

*Margin*.—Entire.

*Texture*.—Glabrous, slightly glossy.

*Color*.—Greyed-green; near RHS 196B, striped purple; near RHS N77C.

*Type*.—Short triangular.

Sepals:

*Quantity*.—Average: 3.

*Appearance*.—One dorsal sepal (pointing upright) and two lateral sepals.

*Length*.—Dorsal sepal approximately 4.8 cm. Lateral sepals approximately 5.5 cm.

*Width*.—Dorsal sepal approximately 4.4 cm. Lateral sepals approximately 5.6 cm.

*Shape*.—Dorsal sepal broad ovate, lateral sepals near orbicular.

*Apex*.—Obtuse.

*Base*.—Cuneate.

*Margin*.—Entire.

*Texture*.—Glabrous, matte, velvety.

*Color*.—Dorsal sepal upper side: green-white (near RHS 157A to 157B), heavily dotted greyed-purple (near RHS N186D). Dorsal sepal under side: Greyed-white (near RHS 156D), veined purple (near RHS 75B), margined greyed-purple (near RHS 186C), sepal dotted greyed-purple near the margins (near RHS 187C). Lateral sepal upper side: greyed-purple (in between RHS N186C and 187B), base slightly dotted yellow-green (RHS 154D). Lateral sepal under side: Yellow-green (in between RHS 145C and 148D), margined and heavily dotted greyed-purple (near RHS N186D).

Pedicels:

*Length*.—Approximately 6.3 cm.

*Diameter*.—Approximately 0.5 cm.

*Angle*.—Approximately 85° angle to peduncle.

*Strength*.—Very strong.

*Texture*.—Glabrous, axially angled with 5 "ribs", axially twisted (due to resupination), glossy.

*Color*.—White; near RHS NN155C, tinged greyed-purple towards the distal end; near RHS 186D, base yellow-green; 146D.

REPRODUCTIVE ORGANS

Stamens, style and stigma fused into column? Yes.

Column length: Approximately 0.8 cm.

Column diameter: Approximately 0.7 cm.

Column color: White; near RHS 155A, striped greyed-purple; 186A.

Ovary:

*Position*.—Inferior.

*Diameter*.—Approximately 0.5 cm.

*Color*.—White; near RHS 155A.

Pollinia color: Yellow-orange; near RHS 14A.

OTHER CHARACTERISTICS

Disease resistance: Neither resistance nor susceptibility to the normal diseases found in *Vanda* has been observed.

Drought tolerance and cold tolerance: Normal for species.

Fruit/seed production: No fruits/seeds detected to date.

What is claimed is:

1. A new and distinct cultivar of *Vanda* plant named 'SPCDW1205' as herein illustrated and described.

* * * * *